United States Patent [19]
Pace

[11] 4,284,078
[45] Aug. 18, 1981

[54] FOUR IN ONE WATER HYGIENE DISPENSER

[76] Inventor: Paul D. Pace, 347 72nd St., Brooklyn, N.Y. 11209

[21] Appl. No.: 130,840

[22] Filed: Mar. 17, 1980

[51] Int. Cl.³ .............................................. A61M 3/00
[52] U.S. Cl. ................................................... 128/229
[58] Field of Search .................. 128/229, 251, 66, 239

[56] References Cited

U.S. PATENT DOCUMENTS

| | | | |
|---|---|---|---|
| 826,172 | 7/1906 | Kintner | 128/229 |
| 1,203,803 | 11/1916 | Speers | 128/229 |
| 1,605,456 | 11/1926 | Mortka | 128/229 X |
| 1,628,733 | 5/1927 | Morris | 128/229 X |
| 1,719,152 | 7/1929 | Watson | 128/229 |
| 2,117,622 | 5/1938 | Morton et al. | 128/229 |
| 2,208,031 | 7/1940 | Hooper | 128/229 |
| 2,984,452 | 5/1961 | Hooper | 128/229 X |

Primary Examiner—John D. Yasko
Attorney, Agent, or Firm—Richard L. Miller

[57] ABSTRACT

An attachment to a water faucet in order that fresh water may be conveniently dispensed for specific uses such as dental hygiene, bath spray, water enema and vaginal douche; the attachment including an adapter at one end of a flexible hose for attachment to a faucet, and various interchangeable adapters attachable to the other end of the hose; the first said adapter including a valve for selectively by-passing the attachment so as to allow the obtaining of water directly from the faucet.

1 Claim, 5 Drawing Figures

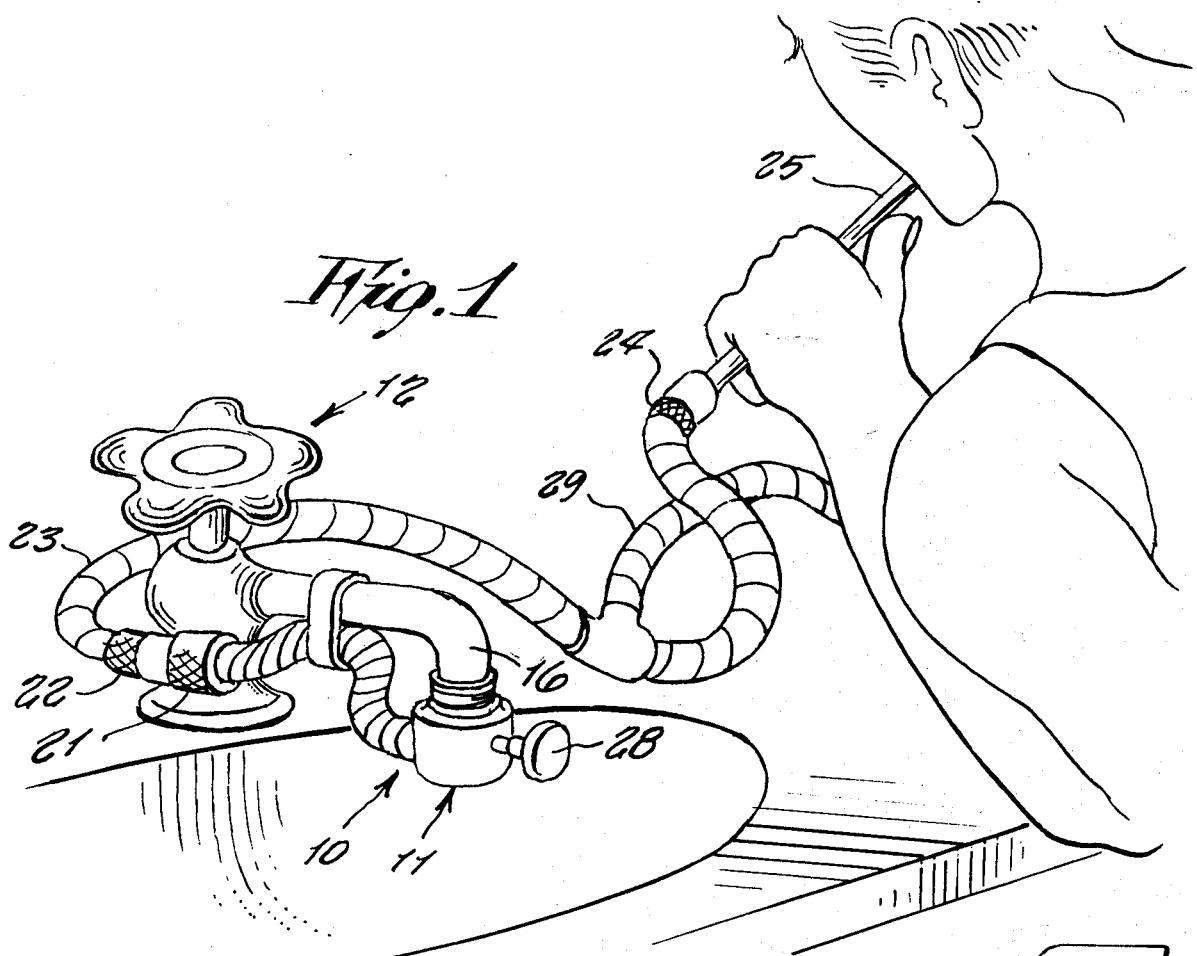
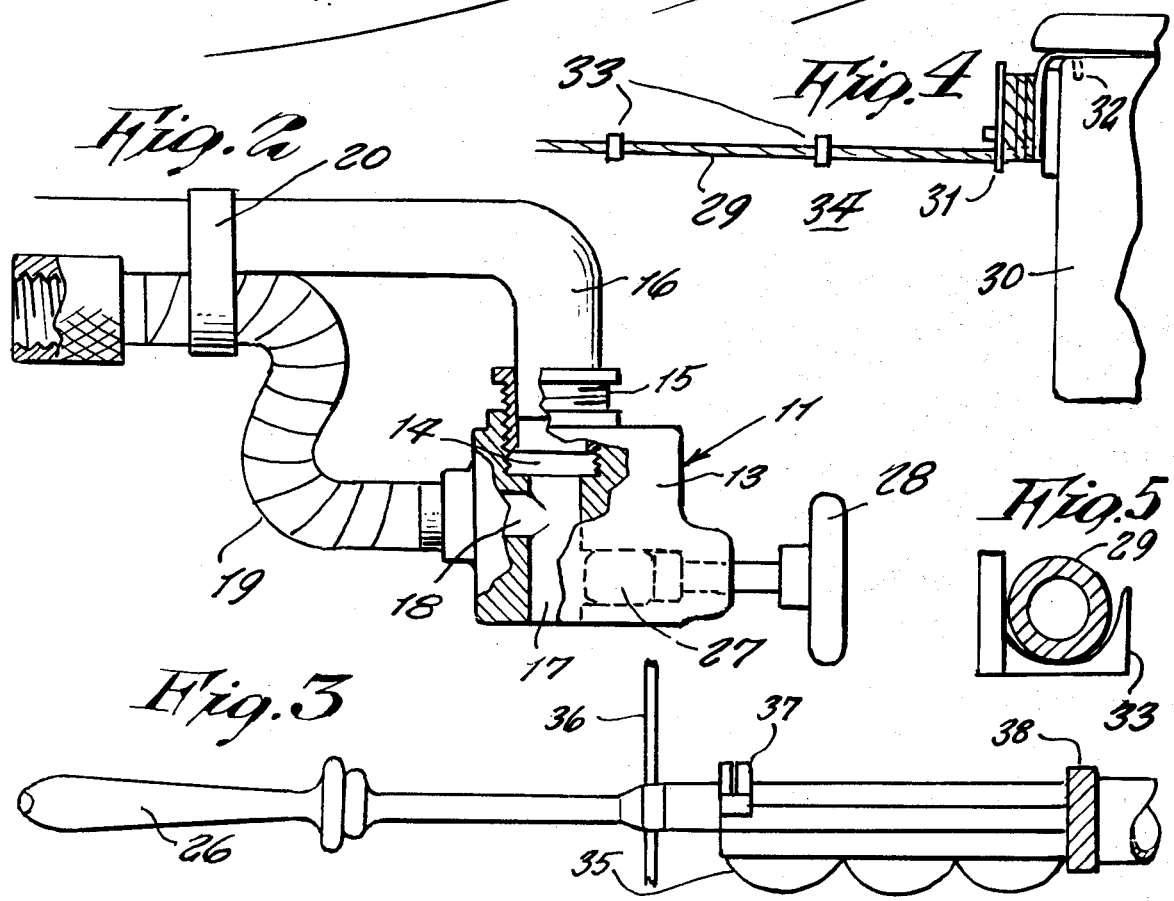

FOUR IN ONE WATER HYGIENE DISPENSER

BACKGROUND OF THE INVENTION

This invention relates generally to water faucet attachments.

It is well known that the use of water directly from a faucet for tasks such as teeth and oral hygiene is not as efficient as it would be if it were delivered directly into a mouth. Most persons use a glass or else simply cup their hand in order to bring water to a mouth for hygiene purposes. This kind of inefficiency also exists when water is splashed directly from a faucet on a body during a bath, instead being poured or sprayed thereupon. Accordingly there is a general need of means to improve such situations where specialized equipment is already not in use.

SUMMARY OF THE INVENTION

Therefore it is a principal object of the present invention to provide a water hygiene dispenser that is attachable to a water faucet, and which includes a hose extension so that it delivers fresh water at any selected water pressure directly to body areas wherever needed.

Another object is to provide a water hygiene dispenser which is particularly adaptable for four different tasks including: teeth and mouth cleaning jet spray, bath spray, clear water enema, and clear water douche for women.

Still a further object is to provide a four in one water hygiene dispenser which will help to prevent tooth decay and mouth odors, help to maintain a cleaner skin and hair so to prevent skin and scalp disorders, prevent vaginal infections, and aid to prevent constipation, gastrointestinal gas, hemorrhoids, colon and rectum cancers, diverticulitis and appendicitis.

Still a further object is to provide a four in one water hygiene dispenser which is made as a kit with interchangeable nozzles for different specific uses.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

FIG. 1 is a perspective view of the invention installed on a faucet.

FIG. 2 is an enlarged detail thereof shown partly in cross section.

FIG. 3 is a side view of one of the attachments.

FIG. 4 is a side view showing a rack for holding attachments of the invention on a toilet water closet.

FIG. 5 is an enlarged end view of a hook used for holding a hose of the invention.

DETAILED DESCRIPTION OF THE PREFERRED EMBODIMENT

Referring now to the drawing in greater detail, the reference numeral 10 represents a four in one water hygiene dispenser, according to the present invention wherein there is an adapter 11 designed for snug fit attachment on a conventional water faucet 12 such as that of a bathroom sink or bathtub. The adapter includes a main body 13 having a threaded entry port 14 into which is screwed a threaded collar 15 that fits around the faucet spout 16 and makes a water tight connection by being tightly screwed together. A vertical passage 17 aligned with the entry port, extends downward through the body so as to allow water to be directly dispensed therefrom. A sideward passage 18 branches from the passage 17 so as to form an outlet port to which is attached to one end of a flexible metal conduit 19 such as a spiral wound, stainless steel gooseneck, so that it may be bent into any direction without being constricted even when a clamp or clip 20, is placed therearound securing the conduit to a side of the faucet spout, as shown in FIGS. 1 and 2, and prevent the conduit hanging down loosely and in a way for other uses of a sink or tub. The conduit accordingly extends rearwardly out of the way and may be relatively short in length.

A coupling 21 is at the opposite end of the conduit, to which a fitting 22 on one end of a flexible rubber hose 23 can be readily screwed. The hose is several feet in length in order that it may reach body areas for various uses, and the hose is wrapped in a spiral wire 23a which prevents the hose from being crushed or bent excessively which would stop the water flow.

An opposite end of the hose 23 has a fitting 24 to which various different nozzles or attachments can be screwed.

One such attachment comprises a toothbrush 25 which allows fresh water to be delivered to the brush bristles for rinsing the teeth clean of toothpaste after a brushing action. This or other attachments (not shown) may be provided for cleansing the mouth. Other attachments may comprise an assortment of various nozzles such as shown at 26 for use in administering an enema, or a vaginal douche. Still others may comprise various spray heads (not shown) for spraying the body or the hair.

The main body includes a valve 27 controlled by a push button 28 for selectively directing water either through the device to the nozzles, or else by-pass the device by running the water from the faucet directly into the sink or tub., thus eliminating the need to detach the device whenever not used.

As shown in FIG. 1, a branch hose line 29 connects to an intermediate portion of the hose 23 and extends to a toilet water closet 30 where it is reeled up around a rack 31 hung over an edge of the tank by means of rack hooks 32.

A row of hooks 33 may be mounted along the bathroom wall 34 and serve to support the portion of the hose line 29 that extends from the rack 31 and to the hose 23.

The attachment shown in FIG. 3 includes a hand grip 35 having a shield 36 at its front so as to shield a hand from water spray by nozzle 26. An on-off valve button 37 controls the water supply to the nozzle. A water volume control 38 can be pre-set so as to limit the water to the valve. With the installation of this invention there will also be supplied on or near the sink a rack for holding the oral dispenser and its attachments (not illustrated in the drawing).

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

I claim:

1. A water hygiene dispenser comprising an adapter for fixing to a water faucet, said adapter comprising a main body portion having a threaded opening, a substantially vertical passageway in said body portion for passage therethrough of water from the water faucet, and a substantially horizontal passageway in said body portion having a first end in fluid communication with said vertical passageway at a position approximately at the center of said vertical passageway, and a second end remote from said first end; said vertical passageway having a cross-sectional area which is less than the cross-sectional area of said threaded opening, said vertical passageway also having a first end in fluid communication with said threaded opening and a second end remote from said first end and flush with the exterior wall surface of said body portion so that water from the water faucet may exit at said second end; said adapter further having a push button control valve mounted within said main body portion and in operational connection with said vertical passageway, said control valve being mounted on a side of said vertical passageway opposite to the side which is connected to said first end of said horizontal passageway, said control valve also being positioned along said vertical passageway at a location lower than said first end of said horizontal passageway in a direction taken from said first end of said vertical passageway toward said second end of said vertical passageway, said control valve directing the flow of water from the water faucet through said first end of said horizontal passageway when said control valve is in a first extended position, and when in a second retracted position allows for the water from the water faucet to exit through said second end of said vertical passageway; said adapter further comprising a threaded collar for reception in said threaded opening, said threaded collar having an outer cross-sectional area greater than the cross-sectional area of said vertical passageway, said collar being positionable on a water faucet to mount said main body portion thereto; a first hose having a first end mounted to said main body portion at said second end of said horizontal passageway, said first end of said first hose being in fluid communication with said second end of said horizontal passageway, and a second end remote from said first end; a second hose having a first end connected to said second end of said first hose and a second end remote from said first end; means for connecting said first end of said second hose to said second end of said first hose; clip means for attaching said first hose to a water faucet, said clip means being positioned between said first and second ends of said first hose; a special attachment mounted at said second end of said second hose for spraying and directing water to a chosen location; means for connecting said attachment to said second end of said second hose; a third hose having a first end in fluid communication with said second hose at a location between said first and second ends of said second hose, and a second end remote from said first end; a plurality of clip means for mounting said third hose to a wall; a mounting rack for winding thereon a portion of said third hose near said second end, said mounting rack having a clip for attaching said rack to a water closet; and means for connecting said first end of said third hose to said second hose for fluid communication therewith, whereby water from a water faucet may be directed to an attachment.

* * * * *